United States Patent [19]
Barlow et al.

[11] Patent Number: 5,712,137
[45] Date of Patent: Jan. 27, 1998

[54] LAMINATE OF A CULTURE SUBSTRATE ON A CARRIER FOR PRODUCING AN APERTURED WOUND DRESSING

[75] Inventors: Yvonne Margaret Barlow, Sawston; Stephen Michael Lang, Saffron Walden, both of United Kingdom

[73] Assignee: Smith & Nephew PLC, United Kingdom

[21] Appl. No.: 436,839

[22] Filed: May 8, 1995

Related U.S. Application Data

[63] Continuation of Ser. No. 191,057, Feb. 2, 1994, abandoned, which is a continuation of Ser. No. 752,659, Aug. 21, 1991, abandoned.

[30] Foreign Application Priority Data

Mar. 5, 1991 [GB] United Kingdom ............ 9004911

[51] Int. Cl.$^6$ .................. C12N 11/08; C12N 5/00; A61F 13/00
[52] U.S. Cl. .............. 435/180; 424/422; 424/93.7; 435/396; 435/283.1; 602/47
[58] Field of Search ............... 435/180, 240.23, 435/240.24, 240.242, 396, 283.1; 602/47; 424/422, 93.7

[56] References Cited

U.S. PATENT DOCUMENTS

| | | | |
|---|---|---|---|
| 3,992,725 | 11/1976 | Homsy | 3/1 |
| 4,553,272 | 11/1985 | Mears | 623/1 |
| 4,939,151 | 7/1990 | Bacehowski et al. | 435/284 |
| 5,015,584 | 5/1991 | Brysk | 435/240.23 |
| 5,037,378 | 8/1991 | Muller et al. | 600/36 |

FOREIGN PATENT DOCUMENTS

| | | |
|---|---|---|
| 0092302 | 10/1983 | European Pat. Off. |
| 8808448 | 11/1988 | WIPO. |
| 89 03228 | 4/1989 | WIPO. |
| 90 00595 | 1/1990 | WIPO. |

*Primary Examiner*—David M. Naff
*Attorney, Agent, or Firm*—Graham & James LLP

[57] ABSTRACT

A conformable wound dressing is prepared by producing a sub-confluent layer of cultured mammalian cells such as epithelial cells anchored to a surface of a synthetic polymeric film which is hydrophobic, non-inhibitory to cell growth and non-cytotoxic. The polymer may be ethylene-vinyl acetate copolymer or a blend of ethylene-vinyl acetate copolymer and polystyrene, and is preferably subjected to corona discharge to improve cell attachment. The polymeric film may be sterilized with ethylene oxide or by gamma-irradiation. Preferably, the polymeric film is a continuous film containing apertures formed by perforation before or after cell culture to provide an apertured wound dressing. In a preferred embodiment, a laminate is formed containing a sub-confluent layer of mammalian cells anchored to a surface of a continuous film of synthetic polymer having a plurality of thin and thick portions cast on and supported by a carrier layer having a plurality of raised portions. When the carrier layer is separated from the polymer film, the thin portions rupture to form apertures in the film to result in an apertured wound dressing. The layer of mammalian cells is formed on the polymeric film by culturing the cells in contact with the film such as when the film forms one wall of a culture vessel. In a preferred embodiment, the cells are cultured in a vessel having the laminate as one wall.

14 Claims, 2 Drawing Sheets

LAMINATE OF A CULTURE SUBSTRATE ON A CARRIER FOR PRODUCING AN APERTURED WOUND DRESSING

This application is a continuation of application Ser. No. 08/191,057, filed Feb. 2, 1994, now abandoned, which is a continuation of application Ser. No. 07/752,659, filed Aug. 21, 1991, now abandoned.

FIELD OF THE INVENTION

This invention relates to the culturing of mammalian anchorage dependent cells onto a conformable substrate. More particularly the invention relates to the formation of wound dressings suitable for treating for example partial thickness wounds such as burns and skin graft donor sites and to systems for use in the preparation of such dressings.

BACKGROUND OF THE INVENTION

Mammalian cells that are incapable of proliferating in suspended liquid culture but can be made to proliferate on the surface of a substrate are said to be anchorage-dependent.

Epithelial cells, such as keratinocytes, are anchorage dependent. Such cells cultured in the presence of a substrate which is non-inhibitory and non-cytotoxic will multiply in stratified colonies and eventually produce a confluent layer. Cell cultures of this type are used to investigate skin growth and have been used as skin grafts. Various technical papers have been published which describe in vitro techniques for growing skin cells and their subsequent use in the treatment of full-thickness wounds. For example E. Bell et al (J Invest Derm 81; 2s–10s 1983); E. Bell et al (Science 211; 1052–1054 1981); D. Asselineau and M. Pruneiras (Br J Derm 1984 III, Supplement 27, 219–222) and J. F. Burke et al (Ann Surg 94; 413–428 1981).

The ability of cells to anchor to a particular substrate is dependent on the properties of the substrate itself as well as the culturing conditions and the components of the culture medium. Culturing is usually carried out in hard plastic flasks made from a material which is substantially inert to the growth media and is non-cytotoxic to the cells. Polystyrene is a commonly used material for culture flasks.

One of the problems in using hard plastic flasks for the culture of epithelial cells for use as skin grafts is that the sheet of cells normally has to reach confluence before they can be harvested. The time taken to reach confluence may be long. Furthermore the layer of cells is not very strong mechanically and can easily be damaged when the unsupported cells are dislodged and handled unsupported.

It is known that the sheet of cells can be supported after it has been dislodged from the surface in order to facilitate handling and transfer to the wound surface. However this technique does not overcome the problems associated with hard surface cultures or the risks associated with dislodgement of the cells.

Epithelial cells have also been grown on natural materials such as collagen which can then be used directly as a skin replacement. The techniques are described in the papers referred to hereinbefore. Whilst epithelial cells grow well on collagen there are several disadvantages in using such a material. Since collagen is a natural substance it is not well defined and can vary substantially from one batch to another which is clinically undesirable if it is to be used as a skin graft. Collagen is also a difficult material to work with in the laboratory and is a complex and time consuming process to isolate it, making it expensive to produce. A further disadvantage is that because collagen is a protein it cannot be easily sterilised by methods such as steam penetration as it will be denatured. Accordingly it is difficult to store and to keep sterile.

In an attempt to overcome the problems associated with the use of collagen and hard plastic surfaces as cell culture substrates it has been proposed to grow cells on the surface of water-swellable hydrophilic synthetic polymers. The cells are not immersed in the aqueous medium but are grown at the substrate-gaseous interface. The resultant sheet is relatively bulky making it poorly conformable and the cell layer has to be fully confluent before it can be transferred to the wound site which can take a considerable time for example 14–22 days. Such a process is described in PCT Publication. No WO88/08448.

SUMMARY OF THE INVENTION

We have now found it is possible to grow cells on a readily manageable, flexible, conformable substrate wherein the cells are immersed in an aqueous medium and thus avoid the problems associated with cultures grown at the substrate-gaseous interface. Moreover, unlike the prior proposals, it is possible and desirable to transfer a cell layer before it has reached confluence. Moreover still this process is considerably faster than prior proposals taking less than 7 days to reach the transferable stage. Such a dressing therefore offers considerable advantages over the prior art.

It is an object of the invention to provide a wound dressing which comprises a layer of cultured mammalian cells anchored to one surface of a conformable substrate which substrate is a synthetic, polymeric film and which is hydrophobic, non-inhibitory to cell growth, non-cytotoxic.

It is also an object of the invention to provide a system for producing a wound dressing by culturing anchorage dependent mammalian cells comprising a conformable synthetic polymeric film which is hydrophobic, non-inhibitory to cell growth, non-cytotoxic, together with a means for maintaining an aqueous culture mechanism containing said cells in contact with one surface of said film.

DETAILED DESCRIPTION OF THE INVENTION

Figure 1:
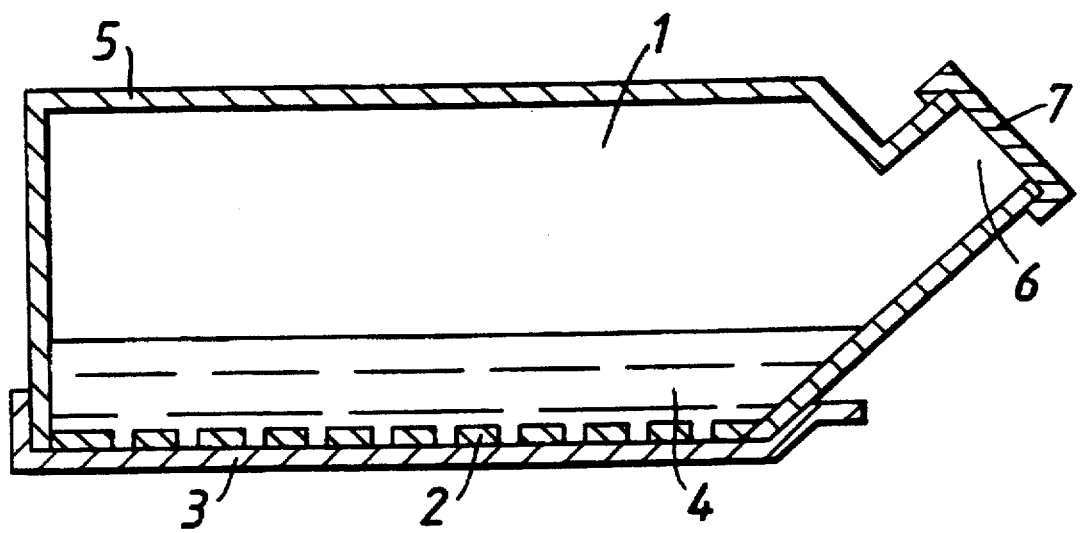
FIG. 1 shows a culture flask where one wall is a laminate of an apertured film on a carrier layer.

In accordance with the present invention there is provided a conformable wound dressing comprising a layer of cultured mammalian cells anchored to one surface of a substrate comprising a film of synthetic polymer and which substrate is hydrophobic, non-inhibitory to cell growth and non-cytotoxic.

The present invention also provides a system for the manufacture of wound dressings comprising a substrate for culturing anchorage dependent mammalian cells and means for maintaining a culture medium in contact with said substrate wherein said substrate is a conformable film of a synthetic polymeric material which is hydrophobic, non-inhibitory to cell growth and non-cytotoxic.

The present invention further provides a method for producing a wound dressing by culturing anchorage dependent mammalian cells onto a substrate contained within the system.

The mammalian cells employed in the present invention are those cells which are anchorage-dependent i.e. they require a substrate onto which they can bind before they are able to proliferate.

By the term 'conformable' we mean that the dressing will conform to changes in dimensions of the body portion to which the dressing is attached.

In order for the substrate to have desirable surface properties which allows the anchorage of the cells the substrate should preferably be a corona-discharge treated film. Corona discharge treatment increases the surface energy of a material and provides improved conditions for cell anchorage. The effect of corona-discharge treatment can be assessed by measuring the contact angle of water on the treated material. A method for measuring contact angle will be hereinafter described. Aptly the contact angle should be reduced by at least 10%, favorably by at least 15% and preferably by at least 20%.

The substrate is a conformable synthetic polymeric film. In order for the substrate to have the flexibility and conformability required for the purposes of the present invention it should suitably have a thickness not exceeding 0.075 mm. More suitably the substrate will have a thickness not exceeding 0.05 mm, and favorably not exceeding 0.04 mm. More favorably the substrate will have a thickness between 0.005 mm–0.03 mm and preferably between 0.010 mm and 0.025 mm for example, 0.015 mm or 0.020 mm.

The substrate is formed from a hydrophobic material. By 'hydrophobic' is meant that the water-uptake does not exceed 15% by weight of the material. More aptly the water uptake should not exceed 10% and favorably it should not exceed 7% by weight of the material. More favorably the water uptake of the substrate should not exceed 5% by weight of the material. Preferably the substrate should not swell at all when in contact with aqueous media.

Percentage water uptake of the substrate is assessed by the following method. A 5 cm×5 cm piece of the substrate is weighed in its dry state. This is then immersed in excess distilled water (at least 100 mls) and left for a period of 24 hours at 20° C. The piece of the substrate is then removed, excess water is allowed to drain and the substrate is re-weighed. The percentage increase in weight obtained is the percentage water uptake.

The substrate should not be inhibitory to cell growth. A measure of such inhibition can be expressed as a percentage cell growth reduction as measured against cells allowed to grow in the absence of a test substrate as hereinafter described. Aptly the substrate should not result in more than 50% reduction in cell growth. More aptly it should not result in more than a 40% reduction in cell growth. Favorably it should not result in more than a 30% reduction in cell growth and preferably not result in more than a 20% reduction in cell growth.

The substrate should not be cytotoxic to cell growth. Cytotoxicity can be measured against a non-cytotoxic control material by a method as hereinafter described. Aptly the cytoxicity of the substrate will not exceed 30%. More aptly the cytotoxicity of the substrate will not exceed 20%. Favorably the cytotoxicity of the substrate will not exceed 20% and preferably it will not exceed 15%.

The substrate may be in the form of a continuous film or an apertured film, for example, formed into a net. Preferably however the substrate is a continuous film which is adapted to be perforated after the cell layer has formed on the substrate.

The use of apertured dressings in accordance with the invention has the advantage that wound exudate, found in a wound covered by a dressing of the invention, can readily escape through the apertures and not build up under the dressings.

Perforation of the film, either before or after cell culture can be carried out by any suitable conventional method such as hot pin perforation or slitting. Perforation after cell growth should be carried with minimum cell disruption and loss. Aptly perforation should give at least a 5% open area and preferably at least 20% open area. Aptly perforation should give less than 50% open area and preferably less than 40% open area. 25% open area is an example.

An especially preferred form of substrate which is adapted to be perforated after cell culture is a continuous film which has been biaxially orientated, for example by drawing and stretching in the machine or transverse direction during manufacture such that when the films are subsequently stretched in the other direction, aperatures are formed therein. Such films are described, for example, in UK-914489, UK-1055963, EP-0141592.

The films forming the substrate may be flat or contoured, for example by embossing. Suitably contoured films may also have apertures. Such contoured materials are described in WO90/00398, for use as coverstocks.

Aptly the continuous films comprising the substrate should be permeable to moisture vapor, oxygen and carbon dioxide. In this way a dressing when in place on the wound will provide moist conditions allowing for the cells to remain viable while the wound heals. The continuous films substrate, while desirably being impervious to liquid water may have a moisture vapor transmission rate (MVTR) not exceeding 2500 $gm^{-2}$ 24 $hrs^{-1}$. More aptly the substrate should have an MVTR not exceeding 1500 $gm^{-2}$ 24 $hrs^{-1}$. Favorably the substrate should have an MVTR not exceeding 1200 $gm^{-2}$ 24 $hrs^{-1}$ and preferably not exceeding 1000 $gm^{-2}$ 24 $hrs^{-1}$. A method for determining the MVTR of a substrate is given as follows:

The moisture vapor transmission rate (MVTR) may be measured by the Payne Cup method. This method uses a cup 1.5 cm deep which has a flanged top. The inner diameter of the flange provides an area of 10 $cm^2$ of material through which moisture vapor may pass. In this method 10 ml of distilled water is added to the cup and a sample of the material under test, large enough to completely cover the flange, is clamped over the cup. When the test material has an adhesive surface it is clamped with the adhesive surface facing into the cup. The complete assembly is then weighed and placed in a fan assisted electric oven where the temperature and relative humidity are maintained at 37° C. and 10% respectively. The relative humidity within the oven is maintained at 10% by placing 1 kg of anhydrous 3–8 mesh calcium chloride on the floor of the oven. After a suitable period of time, for example 17 hours, the cup is removed from the oven and allowed to cool for 20 minutes to reach room temperature. After reweighing,the mass of water lost by vapor transmission is calculated. The moisture vapor permeability is expressed in unit of $gm^{-2}$ 24 $hrs^{-1}$ at 37° C., 100% to 10% relative humidity difference, that is it is the mass of water transmitted through a square meter of material in a 24 hour period when maintained at 37° C. and there are differences of relative humidity at the two surfaces of the material at 100% inside the cup and 10% outside. This is the moisture vapor transmission rate when the film or dressing is in contact with moisture vapor. The moisture vapor transmission rate when the adhesive is in contact with water may be measured using the same apparatus. When the cup is placed in the oven the cup is inverted so that liquid water (and not moisture vapor) is in contact with the test material.

In a modification of the invention the substrate could be formed from knitted or woven polymers to form a tight web of small mesh size. After cell culture the web center can be stretched to form a web having a larger mesh size without loss of cells.

In a further modification still the substrate could comprise two interlocking nets such that the apertures in one net correspond to the strand portions of the other net. The two nets could then be peeled apart post-culture and since both would carry cells they could both be applied to the patient.

Suitable corona-discharge treated polymeric films may have a thickness not exceeding 0.075 mm, a water uptake not exceeding 15%, a percentage reduction in cell growth of not more than 50%, a cytotoxicity of not more than 30% and a moisture vapor permeability not exceeding 2500 $gm^{-2}$ 24 $hrs^{-1}$.

The polymers employed in the present invention are synthetic and do not comprise any naturally occuring polymeric materials or residues. Such synthetic polymers can therefore be produced to a high degree of conformity and consistency. Suitable polymers having for use in the manufacture of the substrates employed in the dressings of invention include copolymers, block copolymers and polymer blends.

Suitable copolymers are those containing vinyl acetate residues such as the ethylene-vinyl acetate copolymers. Suitable ethylene-vinyl acetate copolymers are those containing not more than 20% vinyl acetate. A preferred material, known as EVA 538/539 contains 16% vinyl acetate.

Other suitable polymers include essentially hydrocarbon based materials such as the polybutadienes, polypropylene and polystyrene. Preferred grades of polystyrene include the high impact polystyrenes such as that sold under the trade name STYRON.

Suitable polymers for use in the invention may include block copolymers having hard end blocks and softer mid blocks. Apt block copolymers include styrene based rubbers such as styrene-butadiene-styrene (manufactured by Shell Chemical Co under the trade name CARIFLEX or KRATON).

Another class of polymers suitable for the purposes of the invention are polyesters. A suitable member of this class is polyethylene pterephthalate (manufactured and sold by ICI under the trade name MELINEX).

Polymer blends may also be employed for the substrates of the invention. Preferred materials are blends of ethylene-vinyl acetate with hydrocarbons such as a polyolefin or an aromatic hydrocarbon. A preferred material is a blend of 90% EVA and 10% high impact polystyrene.

Preferably the polymeric film substrate should desirably be transparent in order to allow visualisation of the wound through the dressing.

It is preferred to use autologous cultivated epithelial cells since these have little or no immunological rejection problems when applied to the host (patient). Preferably the cells are keratinocytes. We have found that it is desirable not to allow the cell layer to reach confluence before transferring the wound dressing onto the wound site. Aptly the cells should have reached at least 30% confluence before transfer, favorably at least 40% and preferably at least 50%. It is possible that a suitable wound dressing could be produced within a few hours making the dressing particularly suitable for use as an emergency field dressing when rapid treatment is required.

Preferably the dressing comprises a cell layer which is not more than 2 cells thick, more preferably the cell layer is a monolayer.

The polymeric film substrates can be sterilised by either ethylene oxide (allowing the required time for de-gassing) or by gamma-irradiation. It is important that the polymeric films are washed to remove any low molecular weight contaminants, for example unpolymerised monomer. Such monomers can be cytotoxic and for the reasons given above the substrate should be substantially non-cytotoxic. The washing process may comprise several sequential washes using sterile de-ionised water in sequential steps.

In the system of the invention the substrate on which the cells are grown should preferably be easily removable from the other parts of the system, namely the means for maintaining the aqueous culture medium containing said cells in contact with one surface of the film. For example, where the substrate forms one of the walls of the vessel containing the culture medium, it should be readily removable from the other parts of the vessel. The polymeric film substrate may form a part or all of the container in which the cell culture is grown. The other parts of the container or culture vessel may be formed from suitable materials conventionally used for the manufacture of tissue culture vessels. High impact polystyrene is preferred.

In an alternative embodiment the substrate may be laid down within a flask of an appropriate design adapted to allow the removal of the substrate. Where the substrate is an integral part of the culture flask it may be removably sealed to the other parts of the flask for example by heat sealing or by means of an adhesive. Preferably the substrate will form a flat surface and will aptly form the wall of the flask.

Where the substrate is to be contained within the flask, the flask will be provided with a closeable opening having dimensions sufficient to enable the substrate to be readily removed without disruption of the cells anchored thereto.

Where apertured substrates which are used to form an integral part of the culture flask these may be overlain by continuous film to keep the vessel water tight and to maintain sterility. If the substrate is laid down within the flask or vessel it may be retained by, for example, a pre-sterilised stainless steel ring or, alternatively, by coating the substrate on one side with a layer of non-cytotoxic adhesive which is capable of maintaining tack in the presence of tissue culture medium.

Nutrients, growth factors or medicaments such as antibiotics or antiflammatories may be incorporated into the aqueous medium in which the cell culture is grown. The nature and weight and/or volume of such additional ingredients are conventionally well known.

The wound dressing of this invention is particularly suitable for treating partial-thickness wounds that is those where only the epidermis and possibly part of the dermis is lost. Such wounds include for example skin graft donor sites, first or possibly second degree burns, shallow leg ulcers or pressure sores. Continuous polymeric film substrate aptly act as barriers to bacteria while being sufficiently permeable to moisture vapor, oxygen and carbon dioxide to allow wound healing to occur at a desirable rate. If the substrate is perforated, a secondary dressing could be applied to maintain the desired degrees of moisture vapor, oxygen and carbon dioxide permeabilities. A suitable material is a polyurethane film dressing such as OPSITE (Trade Mark) to create the same conditions. The dressing can suitably be left in place on the wound for a period of up to 7 days allow the wound to become from 30–90% re-epithelialised (healed) depending on the nature of-the particular wound and the condition of the patient. At this time the dressing can be removed and replaced with conventional wound dressings.

The dressings of the present invention offer many advantages over prior art arrangements. Hitherto it has been necessary to culture the layers to a thickness of several cells in order for the cell layer to be handled and manipulated. It was also necessary to grow cell layers to a larger area than required for the dressing since during the conventional enzymatic harvesting techniques the sheet tended to shrink. In addition to the time required to produce a cell sheet which was both large enough to cover the wound and strong enough to be handled, there are additional disadvantages to the use of multi-layer cell sheets. In order to obtain rapid assimilation of the donor sheet into the wound it is highly desirable that the basal surface (which contains actively growing cells) of the cell sheet be in contact with the wound surface. During manipulation of known multi layer cell sheets it is possible for the non-basal layer (where the cells are terminally differentiated) to be the surface in contact with the wound.

With the dressings of the invention it is not necessary, or even desirable to achieve confluence. The dressings of the present invention which comprise a sub-confluent monolayer of cells can be readily produced in a matter of hours, can be readily handled and when presented to the wound will bring actively growing basal cells directly into contact with the host (patient) substrate.

In addition to the foregoing advantages the systems of the invention may utilise cell feed techniques without the disadvantages hitherto associated with these techniques.

In 1975 Green et al proposed the use of transformed cell line 3T3 cells derived from the mouse as a feeder layer system in order to expand skin cultures. 3T3 cells synthesized factors which were essential for the growth of keratinocytes which were seeded at very low densitites and 3T3 cells inhibit fibroblast growth, which are unwanted in skin cell preparation. Skin cell preparation containing 3T3 cells first have to be γ-irradiated (typically about 6000 rads) to inhibit cell division yet not kill the cells. Such cells will survive for several days and during that time will synthesize and supply materials for the host keratinocyte cells. Eventually the 3T3 cells are expelled for the skin cell layer, but inevitably some mouse cells remain and will be grafted with the other host keratinocytes.

In the dressings of the present invention the feeder cells such as 3T3 may be seeded into a medium in contact with the reverse side of the substrate. These cells will then synthesize materials for the host cells. Since the feeder cells do not come into contact with the host cells there is no need to irradiate them. When the substrate is removed from the culture falsk the reverse side may be washed to reverse the free floating feeder cells.

Where a feeder cell layer is employed with an apertured substrate the apertures should be large enough to allow free exchange of the culture media but not large enough to allow cells to pass through. Aptly the aperture size should not be larger than 5 μ across its largest dimenions. Suitably the aperture size will be from 0.5–2 μ.

Embodiments of the dressing systems of the invention will be illustrated by reference to the accompanying drawings. Referring to FIG. 1, one wall of a culture flask 1 comprises a laminate of an apertured film 2 upon a continuous carrier layer 3. The edges of the carrier layer are removably bonded to the other wall portions 5 of the flask 3. Culture media 4 and donor cells can be introduced into flask 3 through neck 6 and sealed therein by stopper 7.

After cell culture, the laminate 2, 3 can be removed by peeling from flask 1. An apertured dressing comprising cells anchored to sheet 2 can be separated from the carrier layer 3 and applied to a patient.

Figure 2:
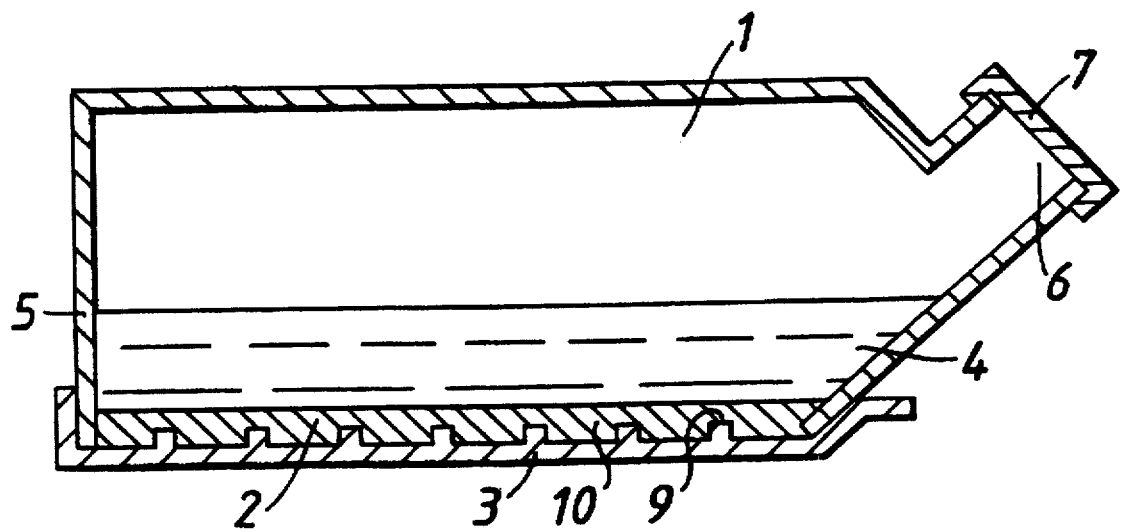
FIG. 2 shows a culture flask where one wall is a laminate of a substrate film having thin and thick portions on a carrier layer having a plurality of raised portions.
Figure 3:
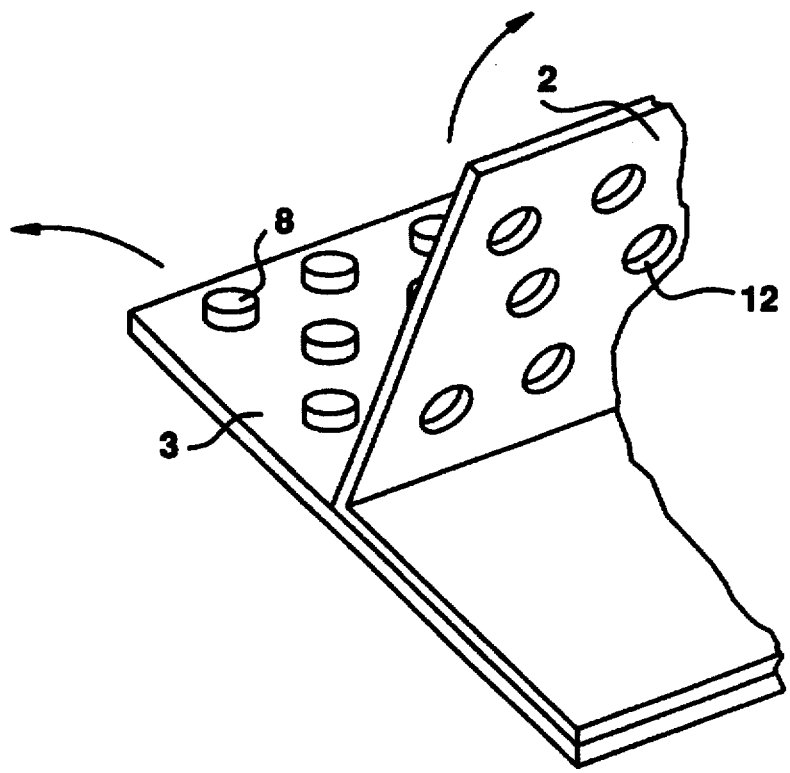
FIG. 3 shows the substrate film containing apertures resulting from separating the film from the carrier layer.

In FIG. 2, the laminate 2, 3 is formed by casting the substrate film 2 over a carrier layer 3 having a plurality of raised portions. The cast substrate layer 2 has a plurality of thin 9 and thickened 10 areas. When the substrate is separated from the carrier layer, the thin areas 9 rupture to form apertures 12 as shown in FIG. 3.

Figure 4:
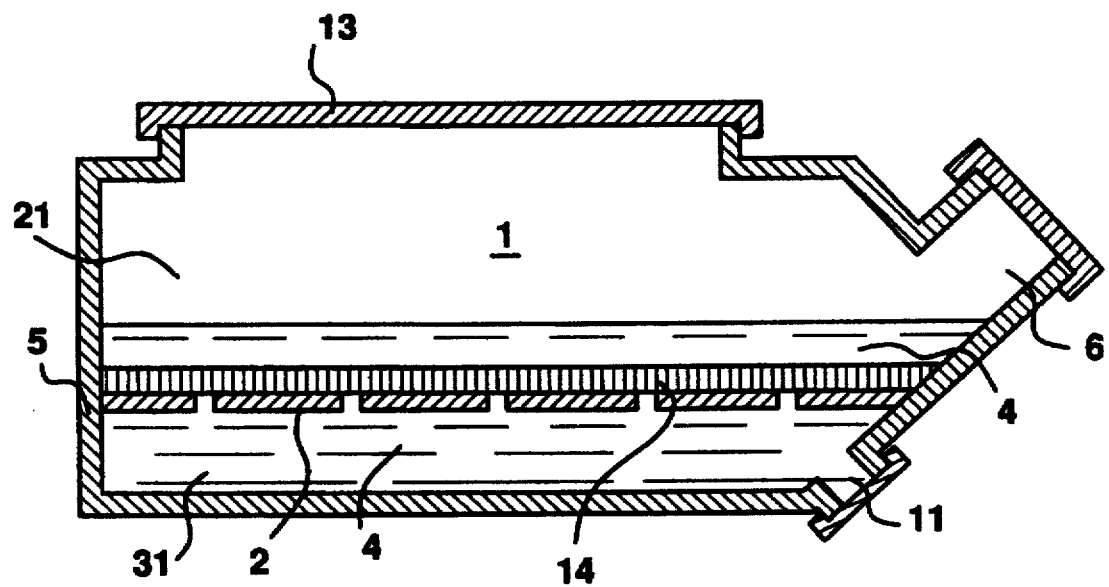
FIG. 4 shows a culture flask where the flask is divided into compartments by a laminate of an apertured film on a carrier layer.

Referring to FIG. 4, the culture flask 1 is divided into compartments 21, 31 by a perforated film 2 comprising the substrate on carrier layer 14. Nutrient media 4 is introduced into the flask and occupies both compartments 21, 31. Skin cells are seeded into compartment 21 through neck 6 while feeder cells such as 3T3 cells are seeded into compartment 31 through access port 11.

After the layer of skin cells 11 has reached the required degree of confluence it is detached from the wall portion 5 of the flask and removed from the access port 13.

Nutrients, growth factors or medicaments such as antibiotics or antiinflammatories may be incorporated into the aqueous medium in which the cell culture is grown. The nature of weight and/or volume of such additional ingredients are conventionally well known.

The invention will now be illustrated by the following Examples wherein the contact angle, cell growth reduction and cytotoxicity were determined as follows:

Measurement of Contact Angles—Surface Energy Determination

Contact angles are measured using a contact angle goniometer as follows:

Each film substrate is layed flat on the goniometer stage. The two contact solutions used are distilled water, dekalin and glycerol. The micrometer screw syringe is filled with distilled water and one drop is allowed to contact the film surface to be measured. At time=0 a photograph of the droplet shape is taken via a camera mounted to the eyepiece of the goniometer. Further photographs are taken periodically (every minute) for approximately ten minutes. The procedure is then repeated using glycerol and dekalin as the contacting medium.

The resultant photographs are then developed. The angle the droplet makes to the horizontal is then measured using a protractor (measured both sides).

Graphs of contact angle versus time are then plotted and the angle at time =0 determined according to the following formula:

surface tension of a liquid=surface free energy ($\gamma$)

Total surface energy ($\gamma$)=$\gamma^d$+$\gamma^p$ $\gamma^d$=dispersive component $\gamma^p$=polar component $$1 + \cos\theta = 2\left[\frac{\left(\gamma^d\left(\frac{1}{2}(\gamma_1^d)\frac{1}{2}\right)\right)}{\gamma_1} + \frac{(\gamma^p)\frac{1}{2}(\gamma_1^p)\frac{1}{2}}{\gamma_1}\right]$$

A Method for Measuring Percentage Cell Growth Reduction

Human epithelial cells (keratinocytes) are seeded onto a substrate or tissue culture plate at a density of $8 \times 10^5$ or $1.5 \times 10^5$ respectively per well in 6 well plates. Cells are cultured in 3 mls of the appropriate media containing 10% foetal calf serum and incubated at 37° C. until they reach approximately 50% confluence. The culture media is then aspirated and the cells re-fed with 3 mls of media containing 0.66 Ci ml$^{-1}$ (specific activity 5.0 Cimmol$^{-1}$) of tritiated thymidine supplied by Amersham International plc. After 18 hours incubation, the media is again aspirated and the substrates removed from their wells. The substrates are then washed extensively with phosphate buffered saline to remove excess tritiated thymidine. The substrates are extracted and then the radioactivity present in trichloroacetic acid insoluble precipitate is measured in a liquid scintillation counter.

The results are expressed as a percentage reduction in tritiated thymidine uptake compared to values obtained in control wells containing no substrate.

A Method for Measuring Percentage Cellular Cytotoxicity of the Substrates

1. Collection of substrate supernatants

Each substrate is set up in duplicate in a 6 well culture plate containing 5 mls of either serum free media or media containing 10% foetal calf serum. After one week's incubation at 37° C. the "substrate supernatants" are collected and frozen at −20° C. until required.

2. Cytotoxicity Assay

Human epithelial cells are seeded at a density of $2 \times 10^4$ cells per well (100 1 volume) into a 96 well culture plate, and incubated at 37° C. until the cells reach confluence. The culture media is then aspirated and media containing 10 Ci ml$^{-1}$ of $^{51}$Cr aqueous sodium dichromate added to the cells. After 24 hours further incubation, the media is aspirated and the cells washed three times with calcium-magnesium free Hanks Balanced Salt Solution to remove excess $^{51}$Cr not taken up by viable cells. Each "Substrate Supernatant" is added to each of four wells in either serum free media or media containing 10% foetal calf serum. 10% foetal calf serum is also added to substrate supernatants which were previously incubated in serum free media. After 24 hours incubation at 37° C. the supernatants are collected and $^{51}$Cr released from dead or damaged cells is measured in a gamma counter.

Baseline measurement of release of $^{51}$Cr from viable cells is measured in serum free media and media containing 10% serum and maximum release of $^{51}$Cr from cells lapsed in 1% sodium dodecyl sulphate. The percentage cellular cytoxicity is measured according to the following formula:

$$\% \text{ Cytotoxicity} = \frac{\text{Experimental release} - \text{baseline release}}{\text{Maximum release} - \text{baseline release}} \times 100$$

EXAMPLE 1

Human Epithelial cells (keratinocytes) were cultured to 50% confluence onto corona-discharge treated discs of 15 cm×12 cm MELINEX film 23 µ thick. Corona discharge was carried out on the film substrate prior to culture using a Sherman C-treater. The C-treater was used manually and set to deliver greater than 50 dynes/cm to the substrate surface. The substrate is placed under the head of the machine and removed slowly in order to achieve this level of treatment.

The culture medium used was based on Green's method as stated in Barlow & Pye (1990) Methods in Molecular Biology Chapter 5 (Humana Press). It consisted of 3 parts DMEM: 1 part F12 containing 10% foetal calf serum and EGF (10 ng ml$^{-1}$), insulin (5 µg ml$^{-1}$), hydrocortisone (0.2 µg ml$^{-1}$), cholera toxin ($10^{-9}$M), transferrin/triiodothyronine (5 µg ml$^{-1}$), ($2 \times 10^{-8}$M) and adenine ($1.8 \times 10^{-4}$M) final concentration. Alternative but equally acceptable media include Keratinocyte Basal Media available from Clonetics & BIORICH Media available from Flow Laboratories. Both of these media are serum free.

The percentage cell growth reduction was found to be 28%.

The percentage cellular cytotoxicity was found to be 7%.

EXAMPLE 2

Example 1 was repeated using corona-discharge treated ethyl vinyl acetate film at 15 µ thickness (EVA 538/539).

The percentage cell growth reduction was found to be 41.5%.

The percentage cellular cytotoxicity was found to be 0%.

The contact angle was found to be 78° on untreated film and 55.5° on corona-discharge treated film.

EXAMPLE 3

Example 1 was repeated using corona-discharge treated polyisobutadiene film at 20 µ thickness.

The percentage cell growth reduction was found to be 33%.

The percentage cellular cytotoxicity was found to be 1%.

The contact angle was found to be 98° on untreated film and 79.5% on corona-discharge treated film.

EXAMPLE 4

Example 1 was repeated using corona-discharge treated ethyl vinyl acetate/high impact polystyrene blends at 20 µ thickness. The following blends gave the results shown.

EVA(28-05)/HIPS 80:20 23% cell growth reduction
and
13% cellular cytotoxicity
EVA539/HIPS 90:10 8% cell growth reduction
and
29% cellular cytotoxicity

EXAMPLE 5

Example 1 was repeated using corona-discharge treated polypropylene film at 20 µ thickness.

The percentage cell growth reduction was found to be 47%.

The percentage cellular cytotoxicity was found to be 8%.

EXAMPLE 6

Example 1 was repeated using corona-discharge treated high impact polystyrene film (STYRON) at 20 µ thickness.

The percentage cell growth reduction was found to be 32%.

The percentage cellular cytotoxicity was found to be 8%.

EXAMPLE 7

Example 1 was repeated using corona-discharge treated styrene-butadiene-styrene rubber film (CARIFLEX 1101) at 20 μ thickness.

The percentage cell growth reduction was found to be 41.5%.

The percentage cellular cytotoxicity was found to be 1%.

EXAMPLE 8

Example 1 was repeated using corona-discharge treated polyvinylidene chloride (PVDC) film at 20 μ thickness.

The percentage cell growth reduction was found to be 27%.

The percentage cellular cytotoxicity was found to be 25%.

EXAMPLES 9–16

Examples 1–8 were repeated but the films were perforated prior to culture using hot-pin perforation techniques to give an open area of 25%. Good cell growth was achieved in all cases with minimal cell loss or perforation.

EXAMPLES 17–24

A system according to FIG. 1 was used to produce a wound dressing. The pre-perforated films used were those as described in Examples 9–16. The cells were grown to 20% confluence (approximately 24–36 hours). The carrier (2) and perforated substrate carrying the cells (1) was detached from the culture vessel (3) and the substrate was then peeled from the carrier. Good cell growth was achieved in all cases.

EXAMPLES 25–32

Examples 17–24 were repeated but instead of pre-perforating the films they were cast onto the base of a flask containing 1 mm stumps according to FIG. 2. After culture the substrate was peeled from the base according to FIG. 3 and was successfully perforated as well as achieving good cell growth in all cases. Cell loss was minimal.

EXAMPLE 33

Example 4 was repeated and the substrate was perforated by stretching according to the method described in European Patent No 0141592. Good cell growth was achieved with no loss of cells upon perforation.

EXAMPLE 34

Example 20 was repeated but the substrate was not pre-perforated. Instead it was stretched according to Example 33 and spontaneously perforated. Good cell growth was achieved with no loss of cells upon perforation.

EXAMPLE 35

A system according to FIG. 1 was used to produce a wound dressing. The net used was as described in PCT Publication No GB090/00398. The cells were grown for approximately 24 hours and the carrier (3) and net (2) carrying the cells were detached from the culture vessel (5). The net was then peeled from the carrier and good cell growth was observed on the net.

EXAMPLE 36

Example 35 was repeated but two sheets of the net were aligned such that the apertures of one net coincided with the continuous portions of the other net. The whole was then sealed to the bottom of the culture vessel (5) and the cells cultured as before. Upon removal from the vessel after 24 hours the two nets were separated and both showed good cell growth. Both nets were then transferred to a patient successfully. Good heating rates and goods host compatibility were observed.

EXAMPLE 37

Examples 1 and 2 were repeated and the resultant dressings were used simultaneously in the treatment of a 3 year old female burns patient. The patient was burned to approximately 40% of body surface area covering the head, one arm, one leg and one side of her body. The patient was grafted on four separate occasions using a combination of split skin grafting and the wound dressing containing the culture cells. The cell culture was derived from an autologous biopsy taken during debridement of the burns patient. The initial seeding density was between $2.5 \times 10^4$ and $6 \times 10^4$ cells per cm$^2$. The culture was grafted approximately 80 hours after the cells were seeded. The substrate film was covered with a secondary dressing comprising a liquid paraffin tulle gras JELONET (Trade Mark) which in turn was covered with crepe bandaging. After 5 days the secondary dressings were removed, the substrate films fell-off with no noticeable adherency and no cells remained on the film. The wounds beneath had healed. No significant difference was observed between the two types of dressing.

We claim:

1. A laminate containing mammalian cells comprising a film substrate supported by a carrier layer, said carrier layer having a plurality of raised portions, and said substrate having a sub-confluent layer of cultured mammalian cells anchored to a first surface thereof, said substrate comprising a continuous film of synthetic polymer material having a plurality of thin and thickened areas, said substrate being cast on the carrier layer and supported by the carrier layer, with said thin areas rupturing to form apertures on separation of said carrier layer from said substrate.

2. A conformable apertured wound dressing for transfer to a wound site comprising an apertured film substrate containing a sub-confluent layer of cultured mamalian cells anchored to one surface of the substrate, said wound dressing being prepared by forming the laminate of claim 1 and separating the carrier layer having a plurality of raised portions from the film substrate containing a sub-confluent layer of cultured cells on a surface and comprising a continuous film of synthetic polymer having a plurality of thin and thick areas, whereby the thin areas rupture on separation to form said apertured wound dressing.

3. A dressing according to claim 1 wherein the cells are epithelial cells.

4. A dressing according to claim 1 wherein the degree of confluence is from 40 to 70%.

5. A dressing according to claim 1 wherein the cell layer is a mono-layer.

6. A dressing according to claim 1 wherein the substrate is moisture vapor permeable.

7. A dressing according to claim 1 wherein the apertured film is formed from a film having weakened areas which upon stretching rupture to form apertures.

8. A dressing according to claim 1 wherein the substrate comprises a corona discharge treated polymer.

9. A dressing according to claim 1 in which the polymer is an ethylene-vinyl acetate copolymer.

10. A dressing according to claim 9 in which the polymer is a blend of an ethylene-vinyl acetate copolymer and a polystyrene.

11. A system for the manufacture of the wound dressings of claim 1, comprising a culture vessel for mammalian cells having as one wall that contacts cells therein a laminate of a film substrate cast on and supported by a carrier layer, said carrier layer having a plurality of raised portions and said film substrate comprising a continuous film of synthetic polymer material having a plurality of thin and thick areas such that said thin areas rupture to form apertures in said film substrate on separation of said carrier layer from said film substrate.

12. A system according to claim 11 wherein the substrate has been subjected to a corona discharge treatment.

13. A system according to claim 11 wherein the synthetic polymer is an ethylene-vinyl acetate copolymer.

14. A system according to claim 13 where the polymer is a blend of ethylene-vinyl acetate copolymer and a polystyrene.

* * * * *